(12) United States Patent
La Thangue et al.

(10) Patent No.: US 6,268,334 B1
(45) Date of Patent: Jul. 31, 2001

(54) PEPTIDE ANTAGONISTS OF DP TRANSCRIPTION FACTORS

(75) Inventors: Nicholas B. La Thangue, Glasgow; Lasantha R. Bandara, Abingdon, both of (GB)

(73) Assignee: Prolifix Limited, Abingdon (GB)

( * ) Notice: Subject to any disclaimer, the term of this patent is extended or adjusted under 35 U.S.C. 154(b) by 0 days.

(21) Appl. No.: 09/308,935

(22) PCT Filed: Dec. 22, 1997

(86) PCT No.: PCT/GB97/03506

§ 371 Date: May 27, 1999

§ 102(e) Date: May 27, 1999

(87) PCT Pub. No.: WO98/28334

PCT Pub. Date: Jul. 2, 1998

(30) Foreign Application Priority Data

Dec. 20, 1996 (GB) .................................................. 9626589

(51) Int. Cl.[7] .......................... A01N 37/18; A61K 38/00; C01K 14/00; C01K 16/00; C01K 17/00
(52) U.S. Cl. ................................................. 514/2; 530/300
(58) Field of Search ............................... 536/23.1; 514/2; 530/300

(56) References Cited

PUBLICATIONS

L.R. Bandara et al.: "Apoptosis induced in mammalian cells by small peptides that functionally antagonise the Rb–regulated E2F transcription factor" Nature Biotechnology, vol. 15, Sep. 1997, pp. 896–901, XP002061239 see the whole document.

L.R. Bandara et al.: "Functional synergy between DP–1 and E2F–1 in the cell cycle–regulating transcription factor DRTF1/E2F" Embo Journal., vol. 12, No. 11, 1993, Eynsham, Oxford GB, pp. 4317–4324, XP002061240 cited in the application see the whole document. See page 4320, column 1, paragraph 3; see p. 4232, column 2, paragraph 3; see p. 4320, column 2, paragraph 2; see figure 2E.

Wu C–L et al: "In Vivo Association of E2F and DP Family Proteins" Molecular and Cellular Biology, vol. 15, No. 5, May 1995, pp. 2536–2546, XP002041648 see figure 1.

D. Derossi et al.: "The third helix of the antennapedia homeodomain translocates through biological membranes" Journal of Biological Chemistry., vol. 269, No. 14, 1994, MD US, pp. 10444–10450, XP002061241 cited in the application see the whole document.

Wu et al., In Vivo Association of E2F and DP Family Proteins, Molecular and Cellular Biology, vol. 15, No. 2, p. 2536–2546, May 1995.*

Girling et al., A new component of the transcription factor DRTF1/E2F, Nature, Vol. 362, p. 83–87, Mar. 1993.*

Dermer, Another Anniversary for the War on Cancer, Bio/Technology, vol. 12, p. 320, May 1995.*

* cited by examiner

Primary Examiner—Anthony C. Caputa
Assistant Examiner—Jennifer Hunt
(74) Attorney, Agent, or Firm—Nixon & Vanderhye P.C.

(57) ABSTRACT

The invention provides a polypeptide consisting essentially of a sequence corresponding to residues 163 to 199 of DP-1 as shown in the Figure, and fragments and variants thereof capable of antagonising the heterodimerization of a DP protein with an E2F protein. Such peptides may be used to induce apoptosis in a cell by introducing into the cell an effective amount of said peptide. Such cells include cardiovascular cells, and the peptide may be delivered in a stent to treat or prevent restinosis.

10 Claims, 3 Drawing Sheets

|     |          |                                          | Activity |     |
|-----|----------|------------------------------------------|----------|-----|
|     |          | 163 : ........................... 199 :  | Dimer    | DB  |
| H   |          | KNIRRRVYDALNVLMAMNIISKEKKEIKWIGLPTNSA     | +        | +   |
| H1  |          | RRRVYDALNVL                              | –        | –   |
| H2  |          | RRRVYDALNVLMAMNIISK                      | +        | +   |
| H3  |          | NVLMAMNIISKEKKEIKWIG                     | +        | +/– |
| H4  |          | EKKEIKWIGLPTNSA                          | –        | –   |
| H5  |          | RVYDALNVLMAMNIIS                         | +        | +/– |
| H6  |          | RRVYDALNVLMAMN                           | –        | –   |
| H7  |          | YDALNVLMAMNIISKEKKEIKWIGLPTNSA           | +        | +   |
| 18  |          | NESAYDQKNIRR                             | –        | –   |
| 15  |          | NLVQRNRQAEQQARR                          | –        | –   |
| 17  |          | EVERQRRLERIKQKQ                          | –        | –   |

FIG. 1

```
      163                                  199
       :                                    :
H      KNIRRRVYDALNVLMAMNIISKEKKKEIKWIGLPTNSA
H1          RRRVYDALNVL
H2          RRRVYDALNVLMAMNIISK
H3                NVLMAMNIISKEKKKEIKWIG
H4                       EKKKEIKWIGLPTNSA
H5         RVYDALNVLMAMNIIS
H6          RRVYDALNVLMAMN
H7           YDALNVLMAMNIISKEKKKEIKWIGLPTNSA

18     NESAYDQKNIRR
15     NLVQRNRQAEQQARR
17     EVERQRRLERIKQKQ
```

| | Activity | |
|---|---|---|
| | Dimer | DB |
| H | + | + |
| H1 | − | − |
| H2 | + | + |
| H3 | + | +/− |
| H4 | − | − |
| H5 | + | +/− |
| H6 | − | − |
| H7 | + | + |
| 18 | − | − |
| 15 | − | − |
| 17 | − | − |

SEQUENCE LISTING

```
<160> NUMBER OF SEQ ID NOS: 18

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: Synthetic

<400> SEQUENCE: 1

Lys Asn Ile Arg Arg Arg Val Tyr Asp Ala Leu Asn Val Leu Met Ala
 1               5                  10                  15

Met Asn Ile Ile Ser Lys Glu Lys Lys Glu Ile Lys Trp Ile Gly Leu
            20                  25                  30

Pro Thr Asn Ser Ala
        35

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic

<400> SEQUENCE: 2

Asn Val Leu Met Ala Met Asn Ile Ile
 1               5

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic

<400> SEQUENCE: 3

Arg Arg Arg Val Tyr Asp Ala Leu Asn Val Leu Met Ala Met Asn Ile
 1               5                  10                  15

Ile Ser Lys

<210> SEQ ID NO 4
<211> LENGTH: 20
<212> TYPE: PRT
```

<213> ORGANISM: Artificial Sequence
<220> FEATURE:
<223> OTHER INFORMATION: Description of Artificial Sequence: Synthetic

<400> SEQUENCE: 4

Asn Val Leu Met Ala Met Asn Ile Ile Ser Lys Glu Lys Lys Glu Ile
 1               5                  10                  15

Lys Trp Ile Gly
            20

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic

<400> SEQUENCE: 5

Arg Val Tyr Asp Ala Leu Asn Val Leu Met Ala Met Asn Ile Ile Ser
 1               5                  10                  15

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic

<400> SEQUENCE: 6

Tyr Asp Ala Leu Asn Val Leu Met Ala Met Asn Ile Ile Ser Lys Glu
 1               5                  10                  15

Lys Lys Glu Ile Lys Trp Ile Gly Leu Pro Thr Asn Ser Ala
            20                  25                  30

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic

<400> SEQUENCE: 7

Ala Leu Asn Val Leu Met Ala
 1               5

<210> SEQ ID NO 8
<211> LENGTH: 16
<212> TYPE: PRT
<213> ORGANISM: Drosophila melanogaster

<400> SEQUENCE: 8

Arg Gln Ile Lys Ile Trp Phe Gln Asn Arg Arg Met Lys Trp Lys Lys
 1               5                  10                  15

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic

<400> SEQUENCE: 9

Arg Arg Arg Val Tyr Asp Ala Leu Asn Val Leu
 1               5                  10

-continued

```
<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 10

Glu Lys Lys Glu Ile Lys Trp Ile Gly Leu Pro Thr Asn Ser Ala
 1               5                  10                  15

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic

<400> SEQUENCE: 11

Arg Arg Val Tyr Asp Ala Leu Asn Val Leu Met Ala Met Asn
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 12

Asn Glu Ser Ala Tyr Asp Gln Lys Asn Ile Arg Arg
 1               5                  10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 13

Asn Leu Val Gln Arg Asn Arg Gln Ala Glu Gln Ala Arg Arg
 1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic

<400> SEQUENCE: 14

Glu Val Glu Arg Gln Arg Arg Leu Glu Arg Ile Lys Gln Lys Gln
 1               5                  10                  15

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Mutant
      peptide

<400> SEQUENCE: 15

Arg Arg Arg Ala Tyr Asp Ala Leu Asn Ala Leu Met Ala Met Asn Ile
 1               5                  10                  15

Ile Ser Lys
```

```
<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Mutant
      peptide

<400> SEQUENCE: 16

Arg Ala Arg Val Tyr Ala Ala Leu Asn Val Leu Met Ala Met Asn Ile
  1               5                  10                  15

Ile Ser Lys

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Mutant
      peptide

<400> SEQUENCE: 17

Arg Arg Arg Val Tyr Asp Ala Arg Asn Val Arg Met Ala Met Asn Ile
  1               5                  10                  15

Ile Ser Lys

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
cgtgtctacg atggcggaaa tgtgctaatg                                          30
```

PEPTIDE ANTAGONISTS OF DP TRANSCRIPTION FACTORS

FIELD OF THE INVENTION

The present invention relates to polypeptides derived from a region of the DP-1 transcription factor which interacts with the E2F family of transcription factor, and their use.

BACKGROUND OF THE INVENTION

The orderly progression of the mammalian cell cycle requires the precise and regulated interplay between growth promoting and inhibiting signals. A critical period for integrating growth regulating signals occurs during early cell cycle progression where, given the appropriate conditions, cells progress through the "restriction point" and thereafter become committed to entering into S phase and the division cycle.

The transition from G1 into S phase is governed by a number of proteins with established roles in cell cycle control. One of the principal players in the control process is the retinoblastoma protein (pRb), a protein with known tumour suppressor properties and whose gene is frequently mutated in human tumour cells (1). The Rb protein is believed to influence the transition from G1 into S phase by regulating cellular targets, such as the family of E2F transcription factors (1,2,3,4). Indeed, a considerable body of evidence supports the idea that E2F transcription factors are preeminent physiological targets in growth control mediated by pRb. For example, over expression of E2F can promote entry into S phase and cell cycle arrest imposed by pRb can be overridden by co-expression of E2F proteins (1,5,6,7,8).

The pathway regulated by pRb receives signals from members of the family of cyclin dependent-kinases, known as cdks, which govern cell cycle progression by controlling the activity through phosphorylation of critical substrates, such as pRb (9,10). Of particular importance for early cell cycle control are cyclins A, D and E which together with an appropriate catalytic cdk subunit, are believed to mediate their effects on proliferation in part by phosphorylating pRb and thereby inactivating its growth regulating properties (11,12,13). Although the contribution of each cyclin/cdk kinase to the phosphorylation of pRb is not clear, cyclins of the D class, frequently as a complex with cdk4, appear to regulate early G1 progression, a process which very likely involves the control of pRb activity (12,13,14).

Loss of normal control by pRb, either through direct mutation in Rb and the action of viral oncoproteins, or indirectly by mutation in one of the genes encoding an afferent regulator, causes E2F to be uncoupled from its control mechanisms (2,15,16). The physiological advantage of such a mechanism for an aberrantly proliferating cell can be surmised when the nature of the target genes regulated by E2F is considered, since many of them are required for S phase progression, such as the genes for DHFR, thymidine synthetase and DNA polymerase α, and others which play regulatory roles during the cell cycle, such as cdc2, B-myb and cyclin A (1,3).

E2F has a heterodimeric DNA binding activity which arises when an E2F and a DP family member interact. Five E2F (17, 18, 19, 20, 21, 22, 23, 24, 25) and three DP (26, 27, 28) family members have been characterised which can interact combinatorially to generate an array of sequence specific heterodimers. Although the E2F component of the heterodimer is variable, the DP component appears to be less so with DP-1 being frequently present in many different cell (26,31,32) Binding of pRb (or pRb-related proteins) to the E2F/DP heterodimer impedes trans activation (29,30), possibly by preventing the activation domain from interacting with the basal transcription apparatus.

DESCRIPTION OF THE DRAWINGS

FIG. 1 shows a summary of peptides analyzed.

DISCLOSURE OF THE INVENTION

Figure 2:
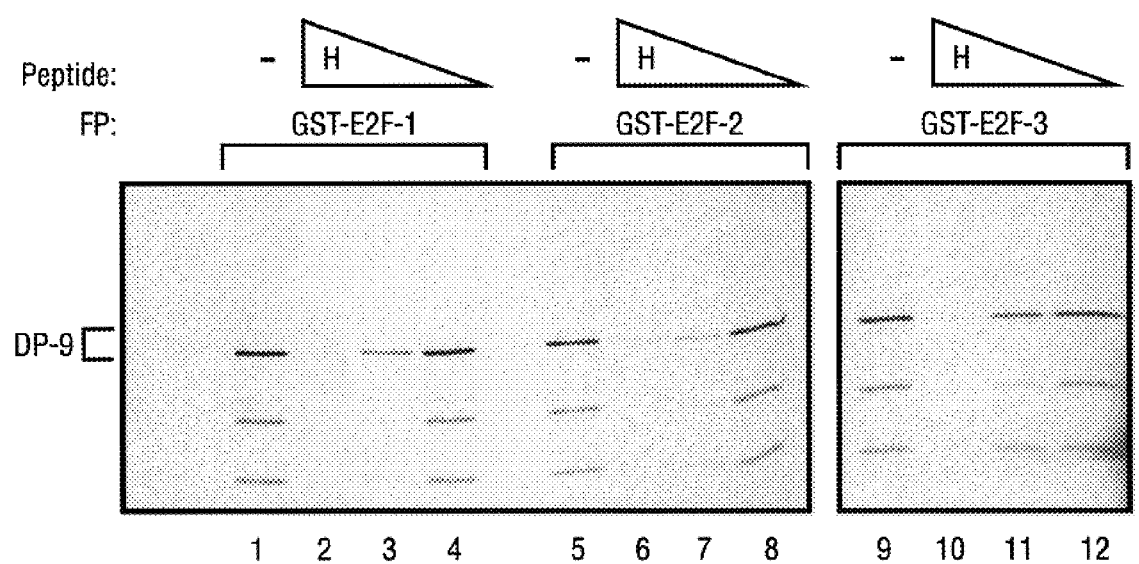
FIG. 2 illustrates that peptides containing DEF box sequence prevent DP-1 forming a heterodimer with E2F family members. The ability of in vitro translated DP-1 (indicated by bracket) to bind to GST-E2F-1 (tracks 1,2,3 and 4), GST-E2F-2 (5,6,7 and 8) or GST-E2F-3 (9,10,11 and 12) in the absence (tracks 1,5 and 9) or presence of decreasing levels of peptide H (5 nmol; tracks 2,6 and 10; 1 nmol tracks 3,7 and 11 or 10 pmol tracks 4,8 and 12).

We have investigated the role of E2F in regulating cell cycle progression by introducing peptides which functionally antagonise E2F activity into proliferating mammalian cells. Peptides representing a conserved region within the DP family of proteins, known as the DEF box, inactivate the DNA binding activity of DP/E2F heterodimers in a variety of assays. Introducing these peptides into mammalian cells causes a rapid onset of apoptosis, a physiological outcome which correlates with the capacity of the peptides to inactivate E2F. The peptides have also been found to cooperate with cytotoxic agents to enhance cell killing. These data define a role for E2F in promoting cellular proliferation, and raise the possibility that small molecules capable of modulating E2F activity may offer a novel therapeutic approach towards controlling aberrant cellular proliferation.

Accordingly, the present invention provides a polypeptide consisting essentially of a sequence corresponding to residues 163 to 199 of DP-1, said sequence being:

KNIRRRVYDALNVLMAMNIISKEKKEIK-WIGLPTNSA (SEQ ID NO:1).

In a further aspect the invention provides a polypeptide fragment of the polypeptide of SEQ ID NO:1 which is capable of antagonising the heterodimerization of a DP protein with an E2F protein.

We have made a number of different polypeptide fragments according to the invention and the fragments made all contain the common sequence NVLMAMNII (SEQ ID NO:2). Therefore in one preferred aspect of the invention the polypeptide fragments all retain this sequence. Polypeptides which retain SEQ ID NO:2 include the following:

RRRVYDALNVLMAMNIISK (SEQ ID NO:3);
NVLMAMNIISKEKKEIKWIG (SEQ ID NO:4);
RVYDALNVLMAMNIIS (SEQ ID NO:5); and
YDALNVLMAMNIISKEKKEIKWIGLPTNSA (SEQ ID NO:6).

In another preferred aspect of the invention we have found that the core region of sequence ALNVLMA (SEQ ID NO:7) is particularly preferred. This sequence is found in the peptides of SEQ ID NOs: 3, 5 and 6 which are thus a preferred aspect of the invention.

In a further aspect of the invention we have made variant polypeptides based on DEF Box polypeptides but which comprise at least one amino acid substitution. Some of these variant polypeptides retain their ability to antagonise the heterodimerization of a DP protein with an E2F protein. Thus the present invention provides variants of the above-mentioned DEF polypeptides which differ from such polypeptides by the presence of from 1 to 5 amino acids substitutions, said variant being capable of antagonising the interaction of DP-1 with E2F-1.

Particular residues which can be substituted include the residues corresponding to positions 167, 169, 171 and 175 of DP-1.

In another aspect of the invention there is provided a fusion polypeptide which comprises a first portion having the amino acid sequence of a polypeptide according to the invention and a second portion, attached to the N- or C-terminus of the first portion, which comprises a sequence of amino acid not naturally contiguous to the first portion in DP-1.

The second polypeptide portion can be any sequence selected by those of skill in the art taking into account the intended purpose of the fusion. For example, the second portion may comprise a detectable tag such as a T7 tag, HA tag or a myc tag allowing identification of the polypeptide in a cell and/or its recovery. The second portion may also be a signal sequence directing expression of the polypeptide from a host cell in which the fusion is being expressed. This will be useful for the recombinant production of polypeptides of the invention.

The second portion may also comprise a molecular tag which influences the overall structure and α-helix can adapt. A number of helix initiators which aid the formation of α-helixes which comprise short peptide sequences are known in the art.

In a preferred embodiment the polypeptide is a membrane translocation sequence, such as the translocation sequence derived from the *Drosophila melanogaster* antennapedia protein. Such membrane translocation sequences are useful in directing entry of the polypeptide of the invention into a cell. The membrane sequence may be the 16 amino acid peptide of SEQ ID NO:8:

Arg-Gln-Ile-Lys-Ile-Trp-Phe-Gln-Asn-Arg-Arg-Met-Lys-Trp-Lys-Lys (SEQ ID NO:8)

This peptide is preferably joined to the N-terminus of E2F-antagonizing polypeptides of the invention.

In an further aspect, the invention provides a pharmaceutical composition comprising a polypeptide according to the invention together with a pharmaceutically acceptable carrier or diluent.

Polypeptides of the invention and compositions thereof may be used for a number of purposes. Such polypeptides are useful as research agents to investigate the interaction between E2F and DP-1. They may be used in positive controls for assays directed to finding further antagonists of E2F-1 and DP-1 heterodimerization. Such assays are described in WO94/10307 and WO96/01425, the disclosures of which are incorporated herein by reference.

In a preferred aspect the polypeptides of the invention may be used in a method of inducing apoptosis in a cell, said method comprising introducing into the cell an effective amount of a polypeptide of the invention. The method may be practised in vitro or in vivo. Where it is practised in vivo the invention will find use in a method treatment of the human or animal body, particularly in methods of treating cancer.

In another aspect of the invention there is provided an expression vector comprising a promoter operably linked to a sequence in coding a polypeptide as defined above. The expression vector can be introduced into a host cell which is compatible with the origin of replication and/or the promoter of said vector.

DETAILED DESCRIPTION OF THE INVENTION

A(i). Polypeptides

In a first embodiment of the invention, there is provided the polypeptide consisting essentially of SEQ ID NO:1. By "consisting essentially" it is meant that the sequence is not, to any significant degree, part of a larger peptide sequence, e.g. the DP-1 polypeptide. This is not however to exclude entirely the presence of a small number, e.g. from 1 to 5 amino acid residues at the N- or C-terminus where the presence of such residues have no significant effect on the function of the polypeptide.

As indicated above, in addition to the polypeptide of SEQ ID NO:1 the invention extends to polypeptides which are fragments of SEQ ID NO:1 which retain the ability to antagonize the heterodimerization of a DP protein with an E2F protein.

By "antagonize the heterodimerization" it is meant that the peptide will have a measurable, specific and titratable effect at least in vitro on the dimerization of a DP protein, preferably a human DP protein and most preferably DP-1, with an E2F protein, preferably a human E2F protein and most preferably human E2F-1. This may be determined by assay methods described in the accompanying examples. More preferably the peptide will be capable of inducing apoptosis in an immortalised mammalian cell in which E2F activity is present.

Desirably, the fragments will have an activity in vitro and/or in vivo which is greater than peptide H3 (SEQ ID NO:4) or H5 (SEQ ID NO:5).

The ability of a polypeptide to antagonize the heterodimerization may be measured by any suitable technique including those shown in the accompanying examples.

A(ii). Variant Polypeptides

We have found that certain amino acid residues of polypeptides based on the DEF box of DP-1 may be substituted without significant loss of the ability of the peptide to antagonize the heterodimerization (as defined above) of a DP protein to an E2F protein. Thus the polypeptides described in A above may be substituted to provide variant polypeptides which form a further aspect of the invention.

Although the number of substitutions which may be made will depend upon the exact size and sequence composition of the portion of the DP-1 163-199 region being varied, in general from 1 to 5 substitutions, preferably from 1 to 3 such as 1 or 2 substitutions may be made.

Positions which may be substituted include 167, 169, 171 and 175. Combinations of these positions may also be substituted. One or more of these positions may be substituted in combination with one, two, three or four other positions.

Substitutions may include conserved substitutions, for example according to the following table, where amino acids on the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Alternatively, any amino acid may be replaced by a small aliphatic amino acid, preferably glycine or alanine.

The ability of variant polypeptides to antagonize the heterodimerization of a DP protein to an E2F protein may be tested in a routine manner as described above in section A.

Variant polypeptides may also modified in any of the ways described herein for polypeptides of the invention. This includes for example "reverse" sequences, synthetic amino acids, modified side chains and labelling. Where methods for the production and use of polypeptides of the invention are described, it will be understood that reference is also being made to variant polypeptides of the invention unless the context explicitly indicates otherwise.

In one aspect, variant polypeptides may be those in which the core regions of SEQ ID NOs:2 and 7, particularly NO:7, are retained unaltered and from 1 to 5 residues in the remaining sequence of SEQ ID NOs:1, 3, 5 or 6 or fragments thereof are substituted.

In another aspect, variant polypeptides may be those in which the core regions of SEQ ID NOs:2 and 7, particularly NO:7, comprise 1, 2 or 3 substitutions which increase the ability of the peptide to antagonize the heterodimerization of the DP-E2F interaction. Such variant polypeptides may include variants of SEQ ID NOs:1, 3, 5 or 6 or fragments thereof in which the non-core residues are either also substituted or are unsubstituted.

B. Production of Polypeptides

Except where specified to the contrary, the polypeptide sequences described herein are shown in the conventional 1-letter code and in the N-terminal to C-terminal orientation. The amino acid sequence of polypeptides of the invention may also be modified to include non-naturally-occurring amino acids or to increase the stability of the compound in vivo. When the compounds are produced by synthetic means, such amino acids may be introduced during production. The compound may also be modified following either synthetic or recombinant production.

Polypeptides of the invention may also be made synthetically using D-amino acids. In such cases, the amino acids will be linked in a reverse sequence in the C to N orientation. This is conventional in the art for producing such peptides.

A number of side-chain modifications for amino acids are known in the art and may be made to the side chains of polypeptides of the present invention. Such modifications include for example, modifications of amino groups by reductive alkylation by reaction with an aldehyde followed by reduction with $NaBH_4$, amidination with methylacetimidate or acylation with acetic anhydride.

The guanidino groups of arginine residues may be modified by the formation of heterocyclic condensation products with reagents such as 2,3-butanedione or glyoxal. Sulphydryl groups may be modified by methods such as carboxymethylation, tryptophan residues may be modified by oxidation or alkylation of the indole ring and the imidazole ring of histidine residues may be modified by alkylation.

The carboxy terminus and any other carboxy side chains may be blocked in the form of an ester group, e.g. a $C_{1-6}$ alkyl ester.

The above examples of modifications to amino acids are not exhaustive. Those of skill in the art may modify amino acid side chains where desired using chemistry known per se in the art.

Polypeptides of the invention may be formulated in the form of a salt. Salts of polypeptides of the invention which may be conveniently used in therapy include physiologically acceptable base salts, eg derived from an appropriate base, such as alkali metal (e.g. sodium), alkaline earth metal (e.g. magnesium) salts, ammonium and $NR_4$ (wherein R is $C_{1-4}$ alkyl) salts. Salts also include physiologically acceptable acid addition salts, including the hydrochloride and acetate salts.

Polypeptides of the invention may be made synthetically or recombinantly, using techniques which are widely available in the art. Synthetic production generally invloves step-wise addition of individual amino acid residues to a reaction vessel in which a polypeptide of a desired sequence is being made. Examples of recombinant techniques are described below.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 90%, e.g. 95%, 98% or 99% of the polypeptide in the preparation is a polypeptide of the invention.

A polypeptide of the invention may be labelled with a revealing label. The revealing label may be any suitable label which allows the polypeptide to be detected. Suitable labels include radioisotopes, e.g. $^{125}I$, enzymes, antibodies, polynucleotides and linkers such as biotin. Labelled polypeptides of the invention may be used in diagnostic procedures such as immunoassays in order to determine the amount of a polypeptide of the invention in a sample.

A polypeptide or labelled polypeptide of the invention or fragment thereof may also be fixed to a solid phase, for example the surface of an immunoassay well or dipstick.

Such labelled and/or immobilized polypeptides may be packaged into kits in a suitable container along with suitable reagents, controls, instructions and the like.

C. Second Portion Sequences

Although the first embodiment of the invention relates to the polypeptide consisting essentially of SEQ ID NO:1, its fragments and variants thereof, the invention also extends to fusion polypeptides comprising the polypeptides described above linked at the N- or C-terminus, or both, to further sequence(s). These further sequence(s) may be selected to provide particular additional functions to the resulting fusion polypeptide. The further sequences do no include sequences which are naturally contiguous to the DP-1 polypeptides, fragments and variants of the invention.

In general the further sequence(s) will not comprise more than a total of 500 amino acids, optionally split between the N- and C-terminus in any proportion. More desirably the sequences will be much shorter, for example not more than 200, preferably not more than 100, for example not more than 50 or even not more than 20 amino acids in total.

The further sequence(s) may be selected by those of skill in the art for a variety of purposes. For example the sequences may be selected to facilitate the recombinant production of polypeptides of the invention. Such sequences will include signal sequences such as the yeast α-factor leader sequence which direct a polypeptide out of a cell.

A further class of sequences are tags which allow the detection of the polypeptide or its recovery by, for example, affinity chromatography. Many such tags are available and include the T7 tag, the HA tag and a myc tag.

Another class of sequences which are preferred are membrane translocation sequences capable of directing the fusion polypeptide through the membrane of a eukaryotic cell. An example of such a sequence is that derived from the *Drosophila melanogaster* antennapedia protein, as illustrated in the accompanying examples.

Other membrane translocation sequences known in the art may be used in an analogous manner.

The membrane translocation sequence may be attached to the N- or C-terminus of the polypeptide of the invention.

Unless the context requires otherwise, reference below to polypeptides of the invention includes the fusion polypeptides described above.

D Pharmaceutical Compositions

Polypeptides, including fusion polypeptides of the invention may be formulated into pharmaceutical compositions. The compositions comprise the polypeptide together with a pharmaceutically acceptable carrier or diluent. Pharmaceutically acceptable carriers or diluents include those used in formulations suitable for oral, topical, or parenteral (e.g. intramuscular or intravenous) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

Suitable liposomes include, for example, those comprising the positively charged lipid (N[1-(2,3-dioleyloxy) propyl]-N,N,N-triethylammonium (DOTMA), those comprising dioleoylphosphatidylethanolamine (DOPE), and those comprising 3β[N-(n',N'-dimethylaminoethane)-carbamoyl]cholesterol (DC-Chol).

Compositions may comprise any desired amount of a polypeptide of the invention. In part this will depend upon the intended formulation and its intended use. By way of general guidance the composition may comprise from about 1% to about 99%, for example from 10% to 90% of a polypeptide of the invention.

The composition may comprise a mixture of more than one, for example two or three, polypeptides of the invention.

We have also found that polypeptides of the invention, when used in conjuction with a second agent capable of inhibiting cell proliferation provides an enhanced anti-proliferative effect. Thus the composition may also comprise other pharmaceutically active ingredients, in particular cytotoxic and/or cytostatic agents.

Alternatively, a polypeptide of the invention may be delivered to a patient in a separate composition from a cytotoxic or cytostatic agent but simultaneously or sequentially. "Sequentially" means that one of the polypeptide or the agent will be delivered first, and the other delivered within a period of time such that the enhanced effect of the two agents together is acheived in a target proliferating cell. Where one or both agents is delivered over a period of time, e.g. through intravenous infusion, the time period of administration of the agents may be sequential or overlapping.

When used in methods of treatment of the human or animal body, the polypeptide and the agent may be administered to a subject at the same site or at different sites.

Thus the invention provides a polypeptide of the invention and a cytotoxic or cytostatic agent for separate or simultaneous use in the treatment of proliferating cells, for example tumour cells, either in vitro or in vivo.

Where in vitro use is contemplated, this will include ex-vivo, e.g. in the treatment of bone marrow from a subject which may be reimplanted into the subject after-treatment.

The invention further provides the use of a polypeptide of the invention for the manufacture of a medicament for the treatment of proliferating cells wherein said cells are also treated, separately or simultaneously, with a cytotoxic or cytostatic agent.

Numerous cytotoxic and/or cytostatic agents are known in the art (e.g. listed in The Merck Index, 12th Edition, 1996) and include:

alkaloids such as etoposide and other toposiomerase inhibitors, paclitaxel, vinblastine and vincristine; alkylating agents such as alkyl sulphonates (e.g. busulfan), aziridines, ethylenimines and methylmelomines (e.g. triethylenemelamine and triethylenephosphoramide), nitrogen mustards (e.g. cyclophosphamide, melphalan and uracil mustard), nitrosoureas and the like;

antibiotics and analogues such as actinomycins, anthramycin, doxorubicin, puromycin and the like;

antimetabolites such as folic acid analogues (e.g. methotrexate), purine analogues (e.g. 6-mercaptopurine and thioguanine) and pyrimidine analogues (e.g fluorouracil);

platinum complexes such as cisplatin; and other anti-neoplastic compounds inculding for example hydroxyurea.

In addition, the cytotoxic or cytostatic compound may be an immunomodulatory compound or hormonal analogue compound. Examples of the former include interferons α, β and γ and interleukins such as IL-2. Examples of the latter include antiandrogens, antiestrogens (e.g. tamoxifen), aromatase inhibitors, estrogen analogues, LHRH analogues (e.g. buserelin) and the like.

Cytostatic compounds also include antimetasatic agents such as matrix metalloproteinase inhibitors such as batimastat.

E. Expression Vectors

In another aspect, the invention provides nucleic acids encoding polypeptides of the invention. Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Preferably, a polynucleotide of the invention in a vector is operably linked to a control sequence which is capable of providing for the expression of the coding sequence by the host cell, i.e. the vector is an expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Such vectors may be transformed into a suitable host cell to provide for expression of a polypeptide of the invention. Thus, in a further aspect the invention provides a process for preparing polypeptides according to the invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell.

A further embodiment of the invention provides host cells transformed or transfected with the vectors for the replication and expression of polynucleotides of the invention. The cells will be chosen to be compatible with the said vector and may for example be bacterial, yeast, insect or mammalian.

Polynucleotides according to the invention may also be inserted into the vectors described above in an antisense orientation in order to provide for the production of antisense RNA. Antisense RNA or other antisense polynucleotides may also be produced by synthetic means. Such antisense polynucleotides may be used in a method of controlling the levels of DP protein in a cell.

Promoters and other expression regulation signals may be selected to be compatible with the host cell for which the expression vector is designed. For example, yeast promoters include *S. cerevisiae* GAL4 and ADH promoters, *S. pombe* nmt1 and adh promoter. Mammalian promoters include the metallothionein promoter which is can be included in response to heavy metals such as cadmium. Viral promoters include the SV40 large T antigen promoter, retroviral LTR promoters and adenovirus promoters. All these promoters are readily available in the art.

The vector may also be adapted to be used in vivo, for example in a method of therapy. Vectors suitable for use in therapy include adenoviral vectors, retroviral vectors and alphavirus vectors. Such vectors are adapted for use in therapy by a number of modifications, for example by making the vector replication defective. Reference may be made to, for example, WO95/14091 for a description of retroviral vectors and WO95/07994 for a description of alphavirus vectors. The disclosures of both references are hereby incorporated by reference.

Vectors for use in therapy will generally be administered in the form of packed viral particles containing the vector, the particles being delivered to the site of a tumour.

F. Assay Methods

The heterodimerization of DP proteins with E2F proteins during the progression of the cell cycle provides a target for the development of therapeutic agents capable of inhibiting uncontrolled cell proliferation, for example found in tumour cells.

A number of assay formats are described in the accompanying examples and in WO94/10307 and WO96/10425. The provision of the polypeptides of the invention provide positive control reagents for such assays which will be desirable in the design of high throughput screening assays for novel compounds which can exert a similar effect. The polypeptides of the invention further provide a basis for rational drug design of pharmaceutical compounds to target the DP/E2F heterodimer.

Polypeptides of the invention are also of use in investigating programmed cell death-apoptosis. While not wishing to be bound by any one theory, our findings indicate that the disruption of the DP protein interaction with an E2F protein may result in apoptosis. The induction of apoptopic cell death is a particularly desirable aim of cancer therapy since this may avoid side-effects associated with cell lysis caused by-some other therapeutic treatments.

The provision of model systems in which apoptosis is inducible allows the study of all aspects of this cell death mechanism and has applications in, for example, oncology and embryology.

Peptides in the present invention may be used in screening assay to define mimotope peptides which behave in an analogous manner to peptides of the invention but which do not have any sequence similarity. A number of assay methods to define peptide interaction with peptides are known. For example, WO86/00991 describes a method for determining mimotopes which comprises making panels of catamer preparations, for example octamers of amino acids, at which one or more of the positions is defined and the remaining positions are randomly made up of other amino acids, determining which catamer binds to a protein of interest and re-screening the protein of interest against a further panel based on the most reactive catamer in which one or more additional designated positions are systematically varied. This may be repeated throughout a number of cycles and used to build up a sequence of a mimotope of interest.

WO89/03430 describes screening methods which permit the preparation of specific mimotopes which mimic the immunological activity of a desired analyte. These mimotopes are identified by reacting a panel of individual peptides wherein said peptides are of systematically varying hydrophobicity, amphipathic characteristics and charge patterns, using an antibody against an antigen of interest. Thus in the present case antibodies against the H2 peptide may be employed and mimotope peptides from such panels may be identified.

Mimotopes obtainable by the above and other methods available in the art form a further aspect of the present invention.

G. Methods of Treatment

Polypeptides of the invention may also be used in methods of treating uncontrolled proliferation of cells. Conditions in which uncontrolled cell proliferation may be treated include psoriasis and the treatment of tumours. Tumour cells include cells of solid tumours such as lung (including small cell lung), bowel (colon), breast, ovarian, prostate, stomach, liver, pancreatic and skin tumours, as well as leukaemias.

In general, the methods will involve administering to a patient in need of treatment an effective amount of a polypeptide (or composition thereof) of the invention. Suitable routes of administration of compounds of the invention include oral or parenteral, and will depend in part upon the intended use and the discretion of the physician. Small peptides may be administered orally although parenteral administration may generally be more convenient in some circumstances.

The amount of polypeptides of the invention administered to a patient is ultimately at the discretion of the physician, taking account of the condition of the patient and the condition to be treated. Typical amounts of polypeptides of the invention required to achieve antagonism of the interaction of a DP protein with an E2F protein will be in the region of from 0.1 $\mu$M to 10 mM, e.g. from 1 $\mu$M to 1 mM in the body of a patient.

Doses may be administered continuously, e.g in the form of a drip, or at discrete intervals, e.g twice daily, daily, weekly or monthly. Doses may also be administered topically to achieve concentrations of active agent on the skin in the ranges described above.

Where a peptide of the invention is to be administered in conduction with a cytotoxic or cytostatic agent, the dose of said agent will be in accordance with manufacturers, instructions.

In a further embodiment, the polypeptides of the invention may be incorporated into a stent which is introduced into the arteries of a patient during an angioplasty procedure. The stent is a hollow metal tube, usually made of stainless steel and optionally coated with a polymeric material such as a plastic which is expanded during the procedure so as to be left in place in the artery to treat heart disease caused by arterial narrowing. A problem with this procedure is the occurrence of restenosis, i.e. the cardiovascular cells tend to grow back and further treatment is ultimately required. By coating the stent with a polypeptide of the invention, the polypeptide is delivered locally into the cardiovascular tissue and will prevent local regrowth of cells by antagonizing entry of the cells through the cell cycle.

Polypeptides of the invention may be either coated onto or incorporated into the stent by conventional means known per se in the art. For example, the polypeptides may be mixed with a pharmaceutically acceptable carrier compatible with the stent material and coated on or into the stent. Where incorporation into the stent is contemplated it is desirable that the stent comprises an open celled polymeric structure. Where the stent is in the form of a mesh, the polypeptides may be incorporated into a suitable delayed release carrier contained in the spaces between the mesh strands. Delayed release formulations are widely available for a number of different purposes in the art; these include formulations based on pharmaceutically acceptable polymers which dissolve slowly in the body following implantation.

A number of coronary stents have been approved for clinical use in the USA by the FDA. These include ballon expandable stents such as the Palmaz-Schatz stent made by Cordis Corporation (a division of Johnson & Johnson Interventional Systems) and the Gianturco-Roubin II (GR-II) stent made by Cook Cardiology (Bloomington, Ind., USA). Self-expanding stents are also used in the art, e.g. the Wallstent (Medinvent-Schneider, Switzerland). Generally these stents are made of a wire of around 0.1 mm (e.g. from 0.07 to 1.5 mm) diameter, are designed to expand to a diameter of 3–5 mm, and are around 10 to 20 mm in length.

Examples of stent coatings to which reference may be made for the provision of peptide coated stents of the invention include a heparin-coated Palmaz-Schatz stent (Serruys et al, Circulation, 1996, 93;412–422) and a platelet glycoprotein IIa/IIIa receptor antibody polymer-coated stent (Aggarwal et al, Circulation, 1996, 94;3311–3317).

For further guidance, those of skill in the art may also make reference to "Coronary Artery Stents", an ACC Expert Consensus Document (Pepine et al, J. Am. Coll. Cardiol., 1996, 28;782–25 794).

The following examples illustrate the invention.

EXAMPLES

A. Resolution of a domain in DP-1 required for the formation of a DP-1/E2F heterodimer.

The region of DP-1 referred to as the DEF box has homology to a corresponding region of E2F-1. The DEF box domain is located in the C-terminal half of the DNA binding domain. The DEF domain is perfectly conserved within other members of the vertebrate DP family, notably DP-2 and DP-3 and the *Drosophila melanogaster* DP homologue (26,27,36), suggesting that this domain may have an important role in dimerization and/or DNA binding of the DP/E2F heterodimer.

To explore these possibilities we took two approaches. In the first, we assessed the effects of small peptides containing DEF box-derived sequence in assays which measured dimerization and DNA binding activity. In the second, we mutated residues within the DEF box in the context of the wild-type DP protein and assessed the activity of the mutant protein in dimerization and DNA binding assays.

The peptides made are illustrated in FIG. 1b which shows the sequence of the indicated peptides analyzed, together with the effects in two biochemical assays, namely the ability of DP-1 to form a heterodimer with an E2F family member (summarised in Dimer column) and interfere with E2F DNA binding activity (summarised in DB column). The numbers relating to peptide H (SEQ ID NO:1) indicate the position of the residues in the DP-1 protein. Peptide 18 (SEQ ID NO:12) contains the N-terminal sequence taken from the DEF homology region, whereas 15 (SEQ ID NO:13) and 17 (SEQ ID NO:14) are taken from DCB1, on the C-terminal side of the DEF homology region.

B. DEF box peptides function as antagonists of the DP-1/E2F heterodimer.

To determine the influence of the DEF box region upon the formation of the DP-1/E2F heterodimer, we used a binding assay in which E2F-1, expressed as a GST-E2F-1 fusion protein, bound to in vitro translated DP-1, an assay used previously to measure dimerization between DP and E2F proteins (31,32). Peptides were included in the binding reaction and their ability to compete with wild-type DP-1 for E2F-1 assessed by the amount of DP-1 which remained bound to the E2F-1 fusion protein.

In the first instance, a peptide encompassing the complete DEF box region, 37 residues in length and referred to as peptide H (SEQ ID NO:1), was found to interfere with the binding efficiency of DP-1 and E2F-1. As peptide H was titrated into the binding reaction a concomitant reduction in the level of DP-1 bound by the E2F-1 fusion protein was apparent (FIG. 2, compare tracks 2 to 4). These data imply that the DEF box region is required for DP-1 to bind to E2F-1.

To evaluate the specificity of this effect, we undertook two controls. Firstly, the effect of DEF box derived peptides on an unrelated but well characterised protein-protein interaction was assessed, namely the binding of pRb to the adenovirus Ela protein (34). The Ela protein, when provided in the assay as an in vitro translate, specifically bound to pRb. The DEF box peptide H had no apparent effect on the interaction. Secondly, unrelated peptides representing other regions of DP-1 or subdomains of peptide H were assessed in the binding reaction. Peptides from different regions of DP-1, notably peptides 15 (SEQ ID NO:13), 17 (SEQ ID NO:14) and 18 (SEQ ID NO:12), failed to have any noticeable effect. Further, the H4 peptides of SEQ ID NO:10 derived from peptide H had no detectable effect. Overall, the results argue that peptide H antagonises the interaction between DP-1 and E2F-1 in the formation of a heterodimer.

Two further series of experiments were performed to gain greater insight into the properties of the peptides. In the first, the size of the DEF box-derived peptide H was reduced in order to define a minimal size necessary for the activity. Peptide H2 (SEQ ID NO:3), representing a 19 residue sequence 30 taken from the N-terminal half of the DEF box, retained wild-type levels of activity. Another peptide, H5 (SEQ ID NO:5), containing 16 residues within H2, likewise retained antagonistic activity whereas shorter peptides, such as H6 (SEQ ID NO:11), lacked activity (summarised in FIG. 1b).

In the second, the activity of the DEF box antagonist peptide H was assessed on heterodimers formed between DP-1 and the other E2F family members, E2F-2 and E2F-3, which show high conservation with E2F-1 across the DEF box. In a similar fashion to its effect on the DP-1/E2F-1 heterodimer, peptide H interfered specifically with the ability of E2F-2 and E2F-3 to bind to DP-1 (FIG. 2, tracks 5 to 12). We conclude therefore that peptides representing sequence derived from the DEF box function as specific antagonists of the DP-1/E2F heterodimer.

C. DEF box peptides disrupt physiological E2F.

Since the peptides function as antagonists of the formation of the DP/E2F heterodimer, we reasoned that they may also interfere with E2F DNA binding activity. To address this question, we determined whether the E2F DNA binding activity created in vitro from combining bacterial DP and E2F fusion proteins was affected by the peptides.

As previously shown, the interaction between DP-1 and E2F-1 leads to co-operative DNA binding activity. Peptide H (SEQ ID NO:1) was titrated into the DP-1/E2F-1 DNA binding assay, using 1 nmol, 0.5 nmol, 0.1 nmol and 0.01 nmol of peptide. Clear inhibition of DNA binding activity was apparent, with some effect discernable at even the lowest peptide concentration. Similar effects were observed with the other peptides, H2 (SEQ ID NO:3), H3 (SEQ ID NO:4), H5 (SEQ ID NO:5) and H7 (SEQ ID NO:6), although H3 and H5 possessed lower activity compared to H2 and H7. In contrast, peptides derived from the DEF box region which failed to affect formation of the DP-1/E2F-1 heterodimer, such as H1 (SEQ ID NO:9), H4 (SEQ ID NO:10) and H6 (SEQ ID NO:11), or unrelated peptides representing other regions of DP-1, such as 15 (SEQ ID NO:13), 17 (SEQ ID NO:14) and 18 (SEQ ID NO:12), did not interfere with DNA binding activity.

Because the DEF box peptides can antagonise DNA binding activity of the DP-1/E2F heterodimer formed in vitro, we went on to establish their effects on physiological E2F. For this experiment, we used extracts prepared from F9 embryonal carcinoma (EC) cells, since these cells contain high levels of endogenous E2F DNA binding activity as a DP-1/E2F- heterodimer (26).

In a similar fashion to its effect upon the in vitro formed activity, the physiological DNA binding activity in F9 EC cell extracts was inactivated upon titration of peptide H (using the same concentrations mentioned above), but not by H1. This effect was specific for E2F since no effect on the unrelated DNA binding activity ATF was observed under similar conditions. These results indicate that the DEF box-derived peptides inactivate physiological E2F DNA binding activity.

It is noteworthy that the slower migrating E2F complex, which contains the pocket protein-E2F complex, was less sensitive to the effects of peptide H relative to the free E2F heterodimer. This view was supported further by studying the peptide effects in extracts prepared from the leukaemic cell line JM which contain high levels of the pRb pocket protein-E2F complex and little free E2F (15), since titration of the DEF box peptides had marginal affects on the pRb-E2F complex. Thus, DEF box-derived peptides preferentially inactivate the free DNA binding activity which is widely believed to be the transcriptionally active form of E2F.

D. Mutations in the DEF box region of the wild-type DP-1 protein.

To study the role of the DEF box region in the context of the wild-type DP-1 protein, we took advantage of a yeast assay previously used to assess the properties of the DP-1/E2F heterodimer (23,31). When assayed in the context of two-hybrid proteins, with DP-1 is fused the LexA DNA binding domain and E2F-1 to the transcriptional activation domain of GAL4, transcriptional stimulation of a reporter construct driven by LEXA DNA binding sites was apparent only when both proteins were expressed together. Similarly, transcriptional activation of a reporter gene driven by physiological E2F DNA binding sites, in p4xWT.CYC1 (23,31), was dependent upon the presence of both proteins.

We used these assays to investigate the importance of the DEF box region, specifically by assessing the effect of altering two residues within the box, notably $A^{172}$ and $L^{173}$, which were changed to glycine residues.

When wild-type DP-1 sequence was replaced with mutant DP-$1^{172/173}$ in the two-hybrid and E2F binding site assays, the activity of DP-$1^{172/173}$ was reduced by about 50% relative to wild-type DP-1 in the two-hybrid assay, indicating that the efficiency of interaction between the two proteins was compromised. This reduction in dimerization efficiency was reflected in the response of the E2F binding site reporter to DP-$1^{172/173}$ which was likewise compromised by about 50%. Thus, the DEF box region of DP-1 is required for the efficient interaction with its heterodimeric partner E2F-1, a result which corroborates the data derived from the earlier peptide competition assays.

To further delineate critical residues within the DEF box, we altered residues within the context of the H2 peptide and thereafter verified their activity in F9 EC cell extracts.

A panel of mutant H2 peptides were assessed in which two residues had been altered. These mutants were:

| | |
|---|---|
| H2mt1: | RRRAYDALNALMAMNIISK (SEQ ID NO:15) |
| H2mt2: | RARVYAALNVLMAMNIISK (SEQ ID NO:16) |
| H2mt3: | RRRVYDARNVRMAMNIISK (SEQ ID NO:17) |

The differences from SEQ ID NO:3 are shown in bold.

The H2mt1 peptide, in which $V^{169}$ and $V^{175}$ were altered, behaved in a similar fashion to the wild-type H2 sequence since it inactivated the E2F site DNA binding activity in F9 EC cell extracts with similar efficiency at a concentration of 1 nmol, thus indicating that these residues play little role in the antagonistic activity of H2. In contrast, H2mt3 failed to retain antagonistic activity since upon addition to the F9 EC cell extract E2F DNA binding activity remained unchanged. Peptide H2mt2 retained some activity, but less than wild-type H2.

E. Physiological consequences of introducing DEF box-derived peptides into mammalian cells.

Since the DEF box region is required for the functional integrity of the DP-1/E2F heterodimer and, further, that DEF box-derived peptides can disrupt endogenous DP-1/E2F heterodimer, introduction of these peptides into mammalian cells provided a means to assess the physiological consequences of inactivating the DP-1/E2F heterodimer. The approach we took was to attach an additional small peptide sequence taken from the Drosophila melanogaster antennapedia protein (35). A peptide containing 16 amino acid residues taken from the third helix of the antennapedia homeodomain protein translocates across biological membranes and has previously been shown to be able to internalise unrelated peptide sequences (35,36).

This domain was attached to peptides H2 (SEQ ID NO:3), H4 (SEQ ID NO:10) and H2mt3 (SEQ ID NO:17) which represent, respectively, a potent antagonist of the DP-1/E2F heterodimer, one lacking any discernable activity and a mutant H2 sequence which has lost activity. The tagged peptides are referred to below as H2*, H4* and H2mt3* respectively. Peptides were introduced into either synchronous cultures of 3T3 cells or asynchronous cultures of cells transformed by over expression of the E2F family member E2F-4 together with DP1 and a mutant Ha-ras oncogene (22).

When asynchronous cultures of either cell-type were treated with 250 nmol of the tagged H2* peptide, a striking visual effect became apparent, beginning at about 5 hours post treatment and continuing thereafter. Notably, the morphology of cells in the culture progressed to a rounder morphology containing granulated nuclei, with a concomitant decrease in cell number. This effect was specific for the tagged H2 peptide H2* since cells treated with H2 (without the additional antennapedia sequence) or tagged H4 peptide (H4*) failed to show any morphological alterations. Importantly, upon introduction of H2mt3* cells with altered morphology were not apparent, indicating that these effects are specific for the wild-type H2 sequence. Further, the morphological changes caused by H2* were apparent in a variety of other cell types, such as C33A, U20S and $10T_{1/2}$.

Having established that the introduction of H2* into cells causes a rapid and gross perturbation in cellular morphology together with altered nuclear integrity, we went on to investigate the physiological processes which may underlie this phenomenon. The altered cellular morphology and nuclei were reminiscent of apoptosis, and several previous studies had noted that experimental manipulation of the E2F pathway can cause alterations in growth rate and, in some cases, induce apoptosis (6,7). Therefore, to test whether the introduction of H2* caused apoptosis, genomic DNA was isolated and assessed for DNA nuclease laddering activity. Laddering activity is induced in cells undergoing apoptosis and can be observed by examining DNA extracted from cells on an agarose gel after subjecting the DNA to electrophoresis on the gel. DNA from cells not undergoing apoptosis remains at the top of the gel. In apoptosing cells, an additional ladder of DNA is observed which has entered the gel.

Genomic DNA extracted from 3T3 cells treated with 1, 5, 10, 100 and 250 nmol of H2* peptide resolyed with a typical laddering profile. Similar laddering profiles were not apparent in either H2 or H4* control treated cells. Furthermore, introduction of the H2mt3* peptide did not cause any laddering activity. These data suggest that the introduction of peptide antagonists which inactivate E2F into proliferating cells activates the apoptopic programme. Based on the biochemical properties determined earlier, it is likely that inactivation of the E2F transcription factor is responsible for this phenomenon.

F. Co-operation between etoposide and E2F inhibitory peptides.

The topoisomerase II inhibitor etoposide is a well known antiproliferative agent which is thought to induce cell death by a cytotoxic mechanism. Since this agent induce cell death by a mechanism distinct from the apoptosis induced by the H2 peptide, we investigated their combined properties in an E2F-derived tumour cell line as a model system for characterising anti tumour agents.

Figure 3:
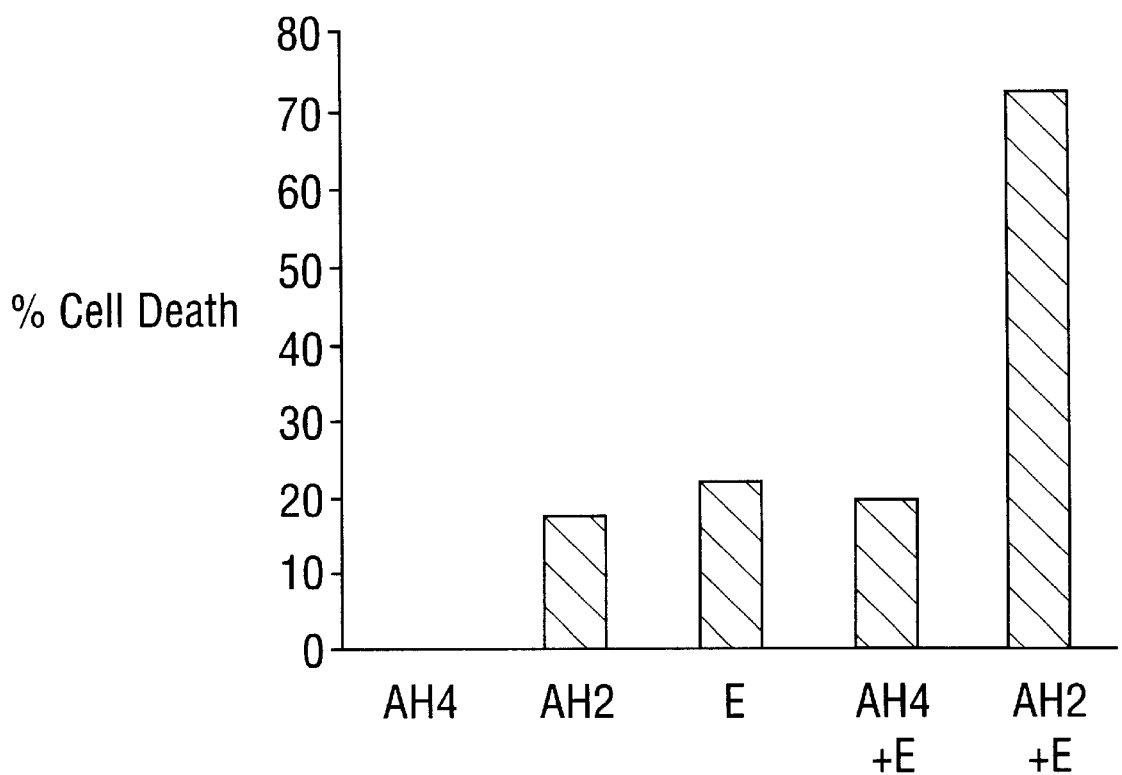
FIG. 3 shows E2F peptides cooperate with etoposide. E2F4 tumour cells were treated with peptides AH2 and AH4 (33 μM) in the absence or presence of etoposide (33 μM). After 24 hours random regions of the culture dish were examined and the percentage of nonviable cells determined by counting cells with an abnormal morphology.

The E2F tumour cell line used in E above was treated with either H2* or H4* peptides alone or in combination with etoposide. At 24 hours post treatment cellular morphology was noted and those with a rounded abnormal appearance were scored as dead. Additional experiments using trypan blue exclusion as a measure of viability yielded similar results. Cultures treated with the H4* peptide showed background levels cell death whereas cultures treated with H2* or etoposide alone showed significantly more death, approximately 15% (FIG. 3). Cultures treated with H2* and etoposide together showed much higher levels of cell death indicating an additive effect of both agents.

Since H2 induces DNA laddering during apoptosis, the integrity of the genomic DNA was assessed at 24 and 48 hours post treatment. After 24 hours DNA damage was observed in H2* treated cultures but not in cells exposed to H4* or etoposide. Although etoposide induced cell death in a similar manner to H2* it did not stimulate DNA laddering consistent with a cytotoxic rather than an apoptotic mechanism of action. Interestingly the amount of DNA laddering in H2*/etoposide treatments was greater than H2* alone, a phenomena which was not apparent in H4*/etoposide treatments. This effect was more evident at 48 hours where the activity of H2* alone was much lower.

Similar cooperative data was obtained with the antimetabolite 5-flurouracil. This is suggestive of a common cytotoxic nonapoptotic pathway to cell death which maybe shared by many antitumour agents.

MATERIALS AND METHODS

The methods used in the Examples were carried out using methodology known as such, adapted for the experiments described above as follows:

Fusion proteins and in vitro translation : GST-E2F-1, E2F-2, E2F-3 and pRb have been described previously (27,31,32) and were purified to homogeneity using glutathione Sepharose. In vitro translated DP-1, DP-1$^{172/173}$ E2F-1 and E1a were translated as described previously (27,31,32).

Gel retardation and binding assays: Gel retardation was performed using 5 to 10 μg of either F9 EC or JM cell extract with either an E2F or ATF site as previously described (15). Where fusion proteins were used, about 25 ng of either DP-1 or E2F-1 were used in each binding assay. For in vitro translates, about 6 μl of the translation mix was used in each binding assay. Gel retardation with an E2F binding site taken from the adenovirus E2a promoter was as previously described (15).

Yeast assays: The yeast two-hybrid expression plasmids used were pLEX(HIS) which contains the complete LexA coding sequence, pGAD.L6 which contains the Gal 4 transcription activation domain. pLEX(HIS) .DP-1 contains the murine DP-1 fused to the C-terminus of the LexA coding sequence and GAD.E2F-1 the human E2F-1 downstream of the Gal4 activation domain; all constructs were as described previously (23,31), apart from pLEX-DP-1/MT which contained DP-1 with residues 172 and 173 altered to glycine residues. Yeast strain CTY10-5d was used for the two-hybrid assay and W3031a, which carries p4xWT.CYC 1, for the E2F site-dependent transcription assay (23,31).

Site-directed mutagenesis: The mutant DP-1 protein, DP-1$^{172/173}$, was made using the Altered Sites in vitro Mutagenesis System (Promega). Briefly, the DP-1 cDNA was ligated into pAlter-1 with the oligonucleotide to incorporate mutant residues being 5'-CGTGTCTACGATGGCGGAAATGTGCTAATG (SEQ ID NO:18). DNA manipulations were carried out according to the manufacturers instructions and all constructs were verified by sequencing.

Peptide introduction into mammalian cells: About 2.5× $10^5$ cells were plated into 6 cm dishes and cultured overnight. Cells were treated with 10 nmol of each peptide in a 2 ml volume and incubated overnight before harvesting. An altered cellular morphology was visualised after 5 hours, becoming apparent in more cells after 16 hours. At 24 hours post treatment, about 20% cells remained viable. For 3T3 cells the peptides were prepared in PBS, whereas for the E2F-transformed cells (22) the peptides were made up in the tissue culture medium.

Isolation of genomic DNA and nuclease-laddering assays: Cultures were harvested in PBS and treated with 0.5% NP40 for 5 minutes. Material harvested by centrifugation was resuspended in TE containing 250 mM EDTA, 0.5% SDS and 100 $\mu$g/ml proteinase K incubated at 37° C. for 3–4 hours. Genomic DNA was then purified and examined by agarose gel electrophoresis.

ETOPOSIDE TREATMENT

Cells were cultured as above. Etoposide (Sigma) was made as a 10 mM stock in DMSO. For cell culture experiments 33 $\mu$M etoposide was used (final conc.) with 33 $\mu$M of peptide.

REFERENCES

1. Weinberg R. A. (1995). The retinoblastoma protein and cell cycle control. Cell 81:323–330.
2. Nevins, J. R. (1992). E2F: a link between the Rb tumor suppressor protein and viral oncoproteins. Science 258:424–429.
3. La Thangue, N. B. (1994). DRTF1/E2F:an expanding family of heterodimeric transcription factors implicated in cell-cycle control. Trends Biochem. Sci. 19:108–114.
4. Lam, E. W.-F, and La Thangue, N. B. (1994). DP and E2F proteins: coordinating transcription with cell cycle progression. Curr. Op. Cell. Biol. 6:859–866.
5. Johnson, D. G., Schwarz. J. K., Cress. W. D., and Nevins. J. R. (1993). Expression of transcription factor E2F1 induces quiescent cells to enter S phase. Nature 365:349–351.
6. Qin X.-Q., Livingston, D. M., Kaelin, W. G. and Adams, P. D. (1994). Deregulated transcription factor E2F-1 expression leads to S-phase entry and p53-mediated apoptosis. Proc. Natl. Acad. Sci. USA 91:10918–10922.
7. Wu, X. and Levine, A. J. (1994). P53 and E2F-1 cooperate to mediate apoptosis. Proc. Natl. Acad. Sci. USA 91:3602–3606.
8. Zhu, L., Van den Heuvel, S., Helin, K., Fattaey, A., Ewen, M., Livingston, D., Dyson, N. and Harlow, E. (1993). Inhibition of cell proliferation by p107, a relative of the retinoblastoma protein. Genes Dev. 7:1111–1125.
9. Sherr, C. J. (1993). Mammalian G1 cyclins. Cell 73:1059–1065.
10. Pines, J. (1995). Cyclins, CDKs and cancer. Seminars in Cancer Biology 6:63–72.
11. Hinds, P. W., Mittnacht, S., Dulic, V., Arnold, A., Reed, S. I. and Weinberg, R. A. (1992). Regulation of retinoblastoma protein functions by ectopic expression of human cyclins. Cell 70:993–1006.
12. Dowdy, S. F., Hinds, P. W., Louie, K., Reed, S. J., Arnold, A. and Weinberg, R. A. (1993). Physical interaction of the retinoblastoma protein with human cyclins. Cells 73:449–511.
13. Ewen, M. E., Sluss, H. K., Sheer, C. J., Matsushime, H., Kato, J. Y. and Livingston, D. M. (1993). Functional interactions of the retinoblastoma protein with mammalian D-type cyclins. Cell 73:487–497.
14. Kato, J., Matsushime, H., Hiebert, S. W., Ewen, M. E. and Sheer, C. J. (1993). Direct binding of cyclin D to the retinoblastoma gene product (pRb) and pRb phosphorylation by the cyclin D-dependent kinases CDK4. Genes Dev. 7:331–342.
15. Bandara, L. R. and La Thangue, N. B. (1991). Adenovirus Ela prevents the retinoblastoma gene product from complexing with a cellular transcription factor. Nature 351:494–497.
16. Chellappan, S. P., Hiebert, S., Mudryj, M., Horowitz, J. M. and Nevins, J. R. (1991). The E2F transcription factor is a cellular target for the Rb protein. Cell 65:1053–1061.
17. Helin, K., Lees, J. A., Vidal, M., Dyson, N., Harlow, E. and Fattaey, A. (1992). A cDNA encoding a pRb-binding protein with properties of the transcription factor E2F. Cell 70:337–350.
18. Kaelin, W. G., Krek, W., Sellers, W. R., DeCaprio, J. A., Ajchanbaum, F., Fuchs, C. S., Chittenden, T., Li, Y., Farnham, P. J., Blanar, M. A., Livingston, D. M. and Flemington, E. K. (1992). Expression cloning of a cDNA encoding a retinoblastoma-binding protein with E2F-like properties. Cell 70:351–364.
19. Shan, B., Zhu, X., Chen, P.-L., Durfee, T., Yang, Y., Sharp, D., Lee, W. H. (1992). Molecular cloning of cellular genes encoding retinoblastoma-associated proteins: Identification of a gene with properties of the transcription factor E2F. Mol. Cell Biol. 12:5620–5631.
20. Lees, J. A., Saito, M., Vidal, M., Valentine, M., Look, T., Harlow, E., Dyson, N. and Helin, K. (1993). The retinoblastoma protein binds to a family of E2F transcription factors. Mol. Cell. Biol. 13:7813–7825.
21. Ginsberg, D., Vairo, G., Chittendon, T., Xiao, Z,-X., Xu, G., Wydner, K. K., De Caprio, J. A., Lawrence, J. B. and Livingston, D. M. (1994). E2F-4, a new E2F transcription factor family member, interacts with p107 and has transforming potential. Genes Dev. 8:2939–2952.
22. Beijersbergen, R. L., Kerkhoven, R. M., Zhu, L., Carlee, L., Voorhoeve, P. M. and Bernards, R. (1994). E2F-4, a new member of the E2F gene family, has oncogenic activity and associates with p107 in vivo. Genes Dev. 8:2680–2690.
23. Buck, V., Allen, K. E., Sorensen, T., Bybee, A., Hijmans, E. M., Voorhoeve, P. M., Bernards, R. and La Thangue, N. B. (1995). Molecular and functional characterisation of E2F-5, a new member of the E2F family. Oncogene 11:31–38.
24. Hijmans, E. M., Voorhoeve, P. M., Beijersbergen, R. L., Veer, L. J. van't and Bernards, R. (1995). E2F-5, a new E2F family member that interacts with p130 in vivo. Mol. Cell. Biol. 15:3082–3089.
25. Sardet, C., Vidal, M., Cobrinik, D., Geng, Y., Onufryk, C., Chen, A. and Weinberg, R. A. (1995). E2F-4 and E2F-5, two members of the E2F family, are expressed in the early phases of the cell cycle. Proc. Natl. Acad. Sci. USA 92:2403–2407.
26. Girling, R., Partridge, J. F., Bandara, L. R., Burden, N., Totty, N. F., Hsuan, J.J. and La Thangue, N. B. (1993). A new component of the transcription factor DRTF1/E2F. Nature 362:83–87.
27. Girling, R., Bandara, L. R., Ormondroyd, E., Lam, E. W.-F., Kotecha, S., Mohun, T. and La Thangue, N. B. (1994). Molecular Characterization of Xenopus laevis DP proteins. Mol. Bio. Cell. 1081–1092.
28. Ormondroyd, E., de la Luna, S. and La Thangue, N. B. (1995). A new member of the DP family, DP-3, with distinct protein products suggests a regulatory role for alternative splicing in the cell cycle transcription factor DRTF/E2F. Oncogene 11:1437–1446.
29. Flemington, E. K., Speck, S. H and Kaelin, Jr. W. G. (1993) E2F-1 mediated transactivation is inhibited by complex formation with the retinoblastoma susceptibility gene product. Proc. Natl. Acad. Sci. USA 90:6914–6918.
30. Helin, K., Harlow, E., Fattaey, A. R., (1993). Inhibition of E2F-1 trans-activation by direct binding of the retinoblastoma protein. Mol. Cell. Biol. 13:6501–6508.
31. Bandara, L. R., Buck, V. M., Zamanian, M., Johnston, L. H. and La Thangue, N. B. (1993). Functional synergy between DP-1 and E2F-1 in the cell cycle-regulating transcription factor DRTF1/E2F. EMBO J. 13:4317–4324.
32. Bandara, L. R., Lam, E. W.-F., Sorensen, T. S., Zamanian, M., Girling, R. and La Thangue, N. B. (1994). DP-1: a cell cycle-regulated and phosphorylated component of transcription factor DRTF1/E2F which is functionally important for recognition by pRb and the adenovirus E4 orf 6/7 protein. EMBO J. 13:3104–3114.
33. Xu, F. H., Alphey, L., Bandara, L. R., Lam, E. W.-F., Glover, D., and La Thangue, N. B. (1995). Functional conservation of the cell cycle-regulating transcription factor DRTF1/E2F and its pathway of control in *Drosophila melanogaster*. J. Cell Science 108:2945–2954.
34. Whyte, P., Buchkovich, K. J., Horowitz, J. M., Friend, S. H., Raybuck, M., Weinberg, R. A. and Harlow, E. (1988). Association between an oncogene and an anti-oncogene: the adenovirus E1A proteins bind to the retinoblastoma gene product. Nature 334:124–129.
35. Derossi D., Joliot A. H., Chassaing G., and Prochiantz A. (1994) The third helix of the antennapedia homeodomain translocates through biological membranes. J.Biol. Chem. 269: 10444–10450.
36. Fahraeus R., Paramio J. M., Ball K. L., Lain S., and Lane D. P. (1996) Inhibition of pRb phosphorylation and cell cycle progression by a 20-residue peptide derived from p16CDKN2/INK4A. Current Biology, vol 6: 84–91.

What is claimed is:

1. A surgical stent which comprises a coating incorporating a polypeptide in a pharmaceutically acceptable carrier, the polypeptide consisting of the amino acid sequence of SEQ ID NO: 3, or a variant thereof having from 1 to 5 amino acid substitutions, the variant retaining the ability to antagonize the formation of a DP/E2F.

2. The stent of claim 1 wherein said variant includes a substitution selected from one or more residues corresponding to residues 167, 169, 171 and 175 of DP-1.

3. The stent of claim 1 wherein said variant consists of the amino acid sequence of SEQ ID NO: 15.

4. The stent of claim 1 wherein said variant consists of the amino acid sequence of SEQ ID NO: 16.

5. A surgical stent which comprises a coating incorporating a polypeptide in a pharmaceutically acceptable carrier, the polypeptide consisting of the amino acid sequence of SEQ ID NO: 3, or a variant thereof having from 1 to 5 amino acid substitutions, the variant retaining the ability to antagonize the formation of a DP/E2F heterodimer, wherein said polypeptide is fused at its N- or C-terminus to a membrane translocation sequence.

6. The stent of claim 5 wherein said membrane translocation sequence is derived from the *Drosophila melanogaster* antennapedia protein.

7. A surgical stent which comprises a coating incorporating a polypeptide in a pharmaceutically acceptable carrier, the polypeptide consisting of the amino acid sequence of SEQ ID NO: 3 and, from 0 to 5 amino acids at the N- or C-terminus, or a variant thereof having from 1 to 5 amino acid substitutions, the variant retaining the ability to antagonize the formation of a DP/E2F heterodimer.

8. The stent of claim 7, wherein said variant includes a substitution selected from one or more residues corresponding to residues 167, 169, 171 and 175 of DP-1.

9. The stent of claim 7, wherein said variant consists of the amino acid sequence of SEQ ID NO: 15.

10. The stent of claim 7, wherein said variant consists of the amino acid sequence of SEQ ID NO: 16.

* * * * *